United States Patent
Helbing

(10) Patent No.: US 7,754,443 B2
(45) Date of Patent: Jul. 13, 2010

(54) SERUM REPLACEMENT FOR THYROID HORMONE-RESPONSIVE CELL CULTURE

(75) Inventor: Caren C. Helbing, Victoria (CA)

(73) Assignee: University of Victoria Innovation and Development Corporation, Victoria, British Columbia (CA)

( * ) Notice: Subject to any disclaimer, the term of this patent is extended or adjusted under 35 U.S.C. 154(b) by 752 days.

(21) Appl. No.: 11/581,144

(22) Filed: Oct. 12, 2006

(65) Prior Publication Data

US 2007/0087329 A1   Apr. 19, 2007

Related U.S. Application Data

(60) Provisional application No. 60/727,129, filed on Oct. 14, 2005.

(51) Int. Cl.
*A61K 35/16* (2006.01)
*C12N 5/00* (2006.01)
*C12N 5/02* (2006.01)
*C12Q 1/02* (2006.01)

(52) U.S. Cl. .................. 435/29; 424/531; 435/404; 435/408

(58) Field of Classification Search .............. None
See application file for complete search history.

(56) References Cited

U.S. PATENT DOCUMENTS 6,599,740 B2 *   7/2003   Sawyer et al. .............. 435/348

* cited by examiner

*Primary Examiner*—David M. Naff
*Assistant Examiner*—Debbie K. Ware
(74) *Attorney, Agent, or Firm*—Klarquist Sparkman, LLP

(57) ABSTRACT

A low thyroid hormone serum supplemented culture medium is provided comprising serum prepared from non-mammalian vertebrates having a developmental stage with low endogenous thyroid hormone ($T_3$ and $T_4$) levels; and a culture medium. The culture medium is for the study of cellular responses to thyroid hormones or chemicals that induce or inhibit a cellular response. Methods of preparation and use are also provided.

Figure 1:
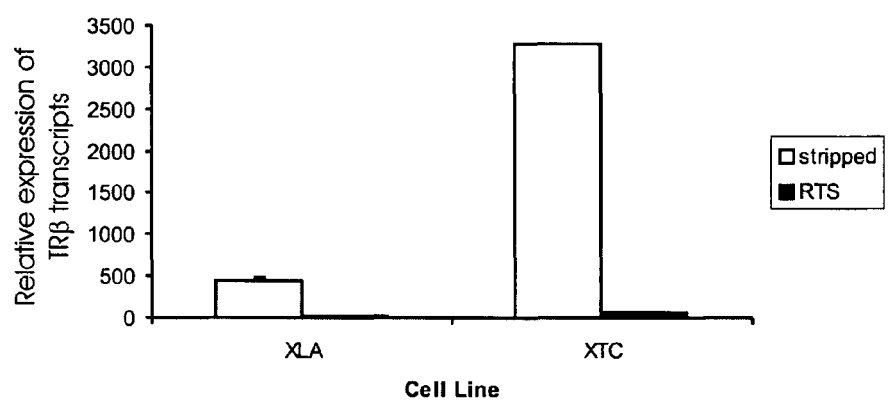
Figure 1:
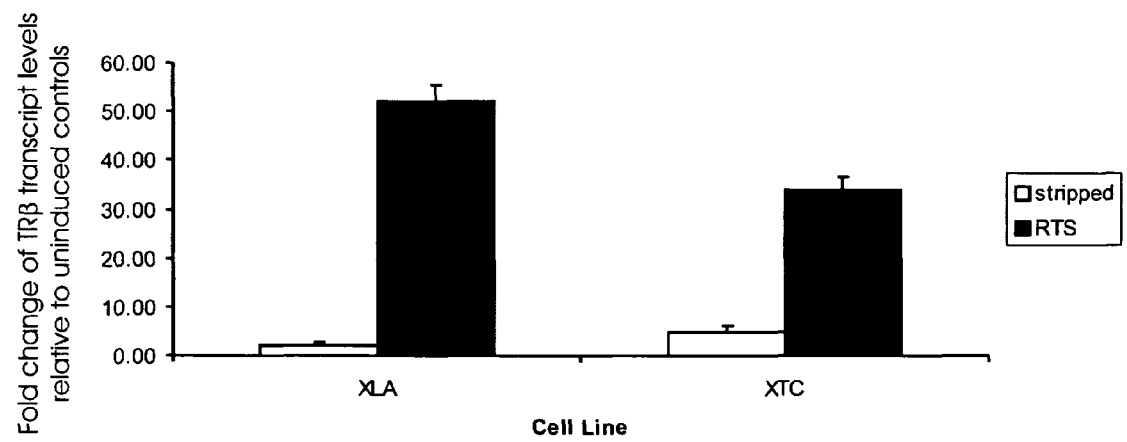

27 Claims, 6 Drawing Sheets

SERUM REPLACEMENT FOR THYROID HORMONE-RESPONSIVE CELL CULTURE

RELATED APPLICATION

This application claims priority to U.S. provisional patent application Ser. No. 60/727,129, filed Oct. 14, 2005, which is incorporated herein by reference.

FIELD

The present embodiment relates to the field of cell culture serum. More specifically, the embodiment relates to a serum that is prepared from non-mammalian vertebrates that undergo a developmental stage that is naturally hypothyroid.

BACKGROUND

Thyroid hormones (TH), 3,5,3'-triiodothyronine (T3) and thyroxine (T4), are essential for growth, development and metabolism. A common way to study TH action is through the use of a wide range of TH-responsive cell lines from mammalian and other vertebrate species (e.g. rat GH3 cells and frog XTC-2 and XLA cells). Typically, these cell lines are maintained in bovine or fetal calf serum which contains sufficient levels of TH to require special treatment ("stripping") of the serum to remove it before TH-dependent effects can be studied.

The stripping method typically requires the use of either activated charcoal or AG1-X10 or AG1-X8 resin (e.g. (Samuels, Stanley et al. 1979)). These methods are proposed for example by Lewis and Parsons U.S. Pat. No. 4,431,741 issued Feb. 14, 1984, Eisentraut U.S. Pat. No. 3,776,698 issued Dec. 4, 1973, Turner et al. U.S. Pat. No. 3,922,145 issued Nov. 25, 1975, and Hollander U.S. Pat. No. 3,928,553 issued Dec. 23, 1975. Unfortunately, these methods are not specific for TH and result in the removal of many other endogenous serum proteins, growth factors and hormones. Alteration of the serum growth medium in this way can influence the growth and survival characteristics of the cells, typically to a detrimental effect. This is exemplified by the fact that TH-responsive cells need to be maintained in regular (TH-containing) serum until a day or two before a TH-induction experiment. The growth medium is then changed to medium containing stripped serum, the cells acclimated to a reduced TH-environment and then TH is added exogenously. Incubation of cells in the stripped medium cannot be accomplished over the long term, because of the lack of necessary growth factors and hormones in the growth medium. The varied removal of these compounds also confounds interpretation and applicability to intact organisms since they themselves influence TH action (Yen 2001).

Production of hypothyroid serum is not easily achieved in mammals, since this represents a serious disease state (Yen 2001). However, there are several other vertebrates that have developmental stages wherein they are naturally in a functionally athyroid state while in a growth intensive phase of their normal development (Norris 1997). Some examples of this occur in frog tadpoles (Regard, Taurog et al. 1978; Kaltenbach 1996), salmonids prior to smoltification (Dickhoff and Sullivan 1987; Specker 1988; Eales and Brown 1993), flatfish (Inui and Miwa 1985), salamanders (Safi, Begue et al. 1997), and lampreys (Youson and Sower 2001).

To illustrate the point further in Amphibia, the larval phase of postembryonic development is primarily a period of extensive growth in the absence of a functional thyroid gland. This premetamorphic phase is followed by a prometamorphic phase in which the thyroid gland matures and low-level secretion of TH occurs (White and Nicoll 1981). TH levels rise and peak at metamorphic climax, which is characterized by the rapid, overt remodeling of the tadpole. It is these growth-intensive periods of development which are conducive to the production of serum with naturally low levels of THs. Low levels of thyroid hormone are considered to be less than approximately 100 ng/dl total T3 or 5 micrograms/dl total T4 as these are the lower end of normal range for humans and cattle (Samuels, Stanley et al. 1979; Shanker, Rao et al. 1984; Health 2005).

Despite the foregoing, there have been no attempts to produce or use serum derived from vertebrates during their athyroid, or low thyroid state. It is an object of the present embodiment to overcome the deficiencies in the prior art.

SUMMARY

The study of cellular responses to thyroid hormones requires the use of a culture medium having all the necessary blood serum components, but lacking thyroid hormone. A process called stripping is employed to remove thyroid hormone from the serum. The present embodiment provides a composition prepared with serum from non-mammalian vertebrates that undergo a developmental stage in which there is little or no thyroid hormone. As the serum from these animals has little or no thyroid hormone, it can be used without stripping.

In one embodiment a composition is provided. The composition comprises a culture medium and serum is from a fish or amphibian at a developmental stage with a low endogenous thyroid hormone level, wherein the composition comprises about 1% to about 25% volume/volume serum, and 10 ng/dl T3 or less and about 0.5 micrograms/dl T4 or less.

In one aspect of the composition, the thyroid hormone comprises T3 and T4.

In another aspect of the composition, the amphibian is at a developmental stage with low endogenous thyroid hormone ($T_3$ and $T_4$) levels.

In another aspect of the composition, the amphibian is a premetamorphic amphibian or a prometamorphic amphibian.

In another aspect of the composition, the amphibian is a frog tadpole.

In another aspect of the composition, the frog is *Rana catesbeiana*.

In another aspect of the composition, the fish is a salmonid parr.

In another aspect of the composition, the salmonid parr is *Salmo salar* (Atlantic salmon).

In another aspect of the composition, the amphibian is a neonate amphibian.

In another aspect of the composition, the neonate amphibian is a salamander *Ambystoma mexicanum* (Mexican axolotl).

In another aspect, the composition comprises about 5 ng/dl T3 or less and 0.25 micrograms/dl T4 or less.

In another aspect, the composition comprises essentially 0 T3 and essentially 0 T4.

In another aspect of the composition, the serum comprises about 100 ng/dl T3 or less and about 5 micrograms/dl T4 or less.

In another aspect of the composition, the serum comprises about 50 ng/dl T3 or less and about 2.5 micrograms/dl T4 or less.

In another aspect of the composition, the serum comprises about 10% (v/v) of the composition.

In another embodiment a method of preparing a composition comprising 10 ng/dl T3 or less and about 0.5 micrograms/dl T4 or less is provided. The method comprises selecting a fish or amphibian at a developmental stage with low endogenous thyroid hormone levels, collecting a low thyroid hormone serum from the vertebrate and mixing the serum with a culture medium to a final concentration of about 1% to about 25% volume/volume serum/culture medium.

In one aspect of the method, the thyroid hormone comprises T3 and T4.

In another aspect of the method, the amphibian is at a developmental stage with low endogenous thyroid hormone ($T_3$ and $T_4$) levels.

In another aspect of the method, the amphibian is a premetamorphic amphibian or a prometamorphic amphibian.

In another aspect of the method, the amphibian is a frog tadpole.

In another aspect of the method, the frog is *Rana catesbeiana*.

In another aspect of the method, the fish is a salmonid parr.

In another aspect of the method, the salmonid is *Salmo salar* (Atlantic salmon).

In another aspect of the method, the amphibian is a neonate amphibian.

In another aspect of the method, the neonate amphibian is a salamander *Ambystoma mexicanum* (Mexican axolotl).

In another aspect of the method, the composition comprises about 5 ng/dl T3 or less and 0.25 micrograms/dl T4 or less.

In another aspect of the method, the composition comprises essentially 0 T3 and essentially 0 T4.

In another aspect of the method, the serum comprises about 100 ng/dl T3 or less and about 5 micrograms/dl T4 or less.

In another aspect of the method, the serum comprises about 50 ng/dl T3 or less and about 2.5 micrograms/dl T4 or less.

In another aspect of the method, the serum comprises about 10% (v/v) of the composition.

In another aspect, the method further comprises stripping the serum.

In another embodiment, a use of low thyroid hormone serum collected from a fish or amphibian at a developmental stage with low endogenous thyroid hormone levels is provided. The use comprises supplementing a culture medium with the serum to provide a composition comprising 10 ng/dl T3 or less and about 0.5 micrograms/dl T4 or less.

In one aspect of the use, culture medium is supplemented with the serum to final concentration of about 1% to about 25% volume/volume serum/culture medium.

In another aspect of the use, the amphibian is a premetamorphic amphibian or a prometamorphic amphibian.

In another aspect of the use, the amphibian is a frog tadpole.

In another aspect of the use, the frog is *Rana catesbeiana*.

In another aspect of the use, the fish is a salmonid parr.

In another aspect of the use, the salmonid parr is *Salmo salar* (Atlantic salmon).

In another aspect of the use, the amphibian is a neonate amphibian.

In another aspect of the use, the neonate amphibian is a salamander *Ambystoma mexicanum* (Mexican axolotl).

In another aspect, the use further comprises measuring a cellular response, for the study of thyroid hormone responsive cells.

In another aspect of the use, the cellular response is TH receptor β (TRβ) gene expression.

In another aspect of the use, the thyroid hormone responsive cells are selected from the group consisting of GH3, GH1, GC, XTC-2, XL-58, XL2, A6, XL177, XLA, XLT-15, and nTERA2 cells.

In another aspect of the use, the thyroid hormone responsive cells are GH3 or XTC-2 cells.

In another aspect of the use, the serum thyroid hormone levels are about 100 ng/dl T3 or less and about 5 micrograms/dl T4 or less.

In another aspect of the use, the serum thyroid hormone levels are about 50 ng/dl T3 or less and about 2.5 micrograms/dl T4 or less.

In another aspect of the use, the serum is collected from non-mammalian vertebrates having essentially no serum thyroid hormone.

In another embodiment, a method of studying cellular responses in thyroid responsive cells is provided. The method comprises:

preparing a composition comprising 10 ng/dl T3 or less and about 0.5 micrograms/dl T4 or less, from serum having endogenous T3 and T4 levels of about 100 ng/dl T3 or less and about 5 micrograms/dl T4 or less, and culture medium to a final concentration of about 1% to about 25% volume/volume serum/culture medium;

culturing the cells in the composition;

adding exogenous T3, T4 or both T3 and T4; and measuring a cellular response.

In one aspect of the method, the cellular response is TH receptor β (TRβ) gene expression.

In another aspect of the method, the thyroid hormone responsive cells are selected from the group consisting of GH3, GH1, GC, XTC-2, XL-58, XL2, A6, XL177, XLA, XLT-15, and nTERA2 cells.

In another aspect of the method, the thyroid hormone responsive cells are GH3 or XTC-2 cells.

In another aspect, the method further comprises adding an at least one chemical that induces or inhibits a cellular response and measuring the cellular response.

FIGURES

FIG. 1 is showing that XLA and XTC frog cells cultured in *Rana catesbeiana* tadpole serum have lower background levels of TRβ mRNA transcript compared to charcoal stripped serum. The indicated cell types were plated at a density of $2 \times 10^4$ cells/cm$^2$ and cultured in the presence of medium containing either 10% charcoal stripped fetal calf serum (stripped) or *Rana* tadpole serum (RTS). After 2 days, 10 nM T3 or vehicle control was added and the cells were harvested 2 days later for quantitative real time-polymerase chain reaction (RT-QPCR) analysis for TRβ transcript levels (indicative of the presence of thyroid hormones). All values were normalized to an invariant L8 ribosomal protein transcript. A) Relative expression levels of the control cells. B) Fold change of the TRβ transcript levels relative to the control, uninduced cells in accordance with an embodiment.

Figure 2:
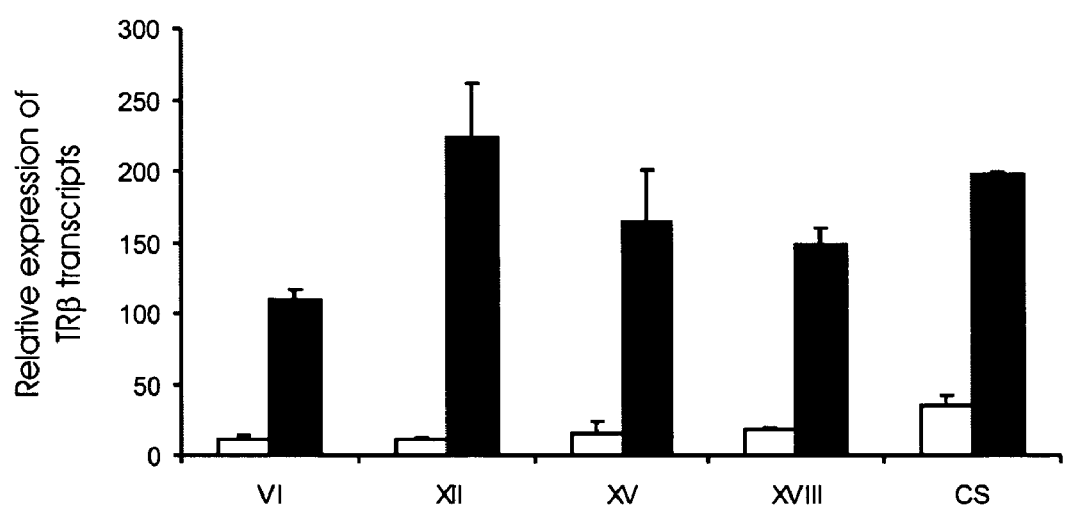

FIG. 2 is showing that cells grown in *Rana* tadpole serum from different developmental stages have lower background levels of TRβ mRNA compared to cells grown in stripped fetal calf serum and display responsiveness to T3. XTC cells were plated in triplicate at a density of $2 \times 10^4$ cells/cm$^2$ and cultured in the presence of medium containing either 10% charcoal stripped fetal calf serum (CS) or *Rana* tadpole serum from different premetamorphic (VI, XII) or prometamorphic (XV, XVIII) stages (Taylor and Kollros, 1946). After 2 days, 10 nM T3 or vehicle control was added and the cells were harvested 2 days later for quantitative real time-polymerase chain reaction (RT-QPCR) analysis for TRβ transcript levels (indicative of the presence of thyroid hormones). All values were normalized to an invariant L8 ribosomal protein transcript. The relative expression levels are indicated with vehicle control (white bars) and T3-exposed (black bars) cells in accordance with an embodiment.

Figure 3:
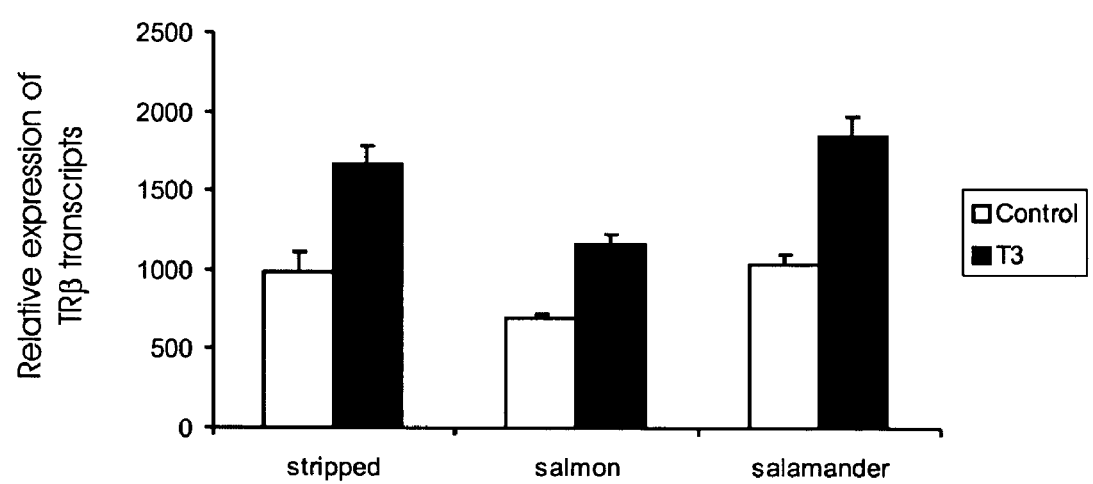

FIG. 3 is evidence that serum from other species is suitable for use in thyroid hormone induction experiments. XTC cells were plated at a density of $2 \times 10^4$ cells/cm$^2$ and cultured in the presence of medium containing either 10% charcoal stripped fetal calf serum (stripped), serum from salmon Parr (salmon), or neotenic salamanders (salamander). After 2 days, 10 nM T3 or vehicle control was added and the cells were harvested 2 days later for quantitative real time-polymerase chain reaction (RT-QPCR) analysis for TRβ transcript levels (indicative of the presence of thyroid hormones). All values were normalized to an invariant L8 ribosomal protein transcript. The relative expression levels are indicated with vehicle control (white bars) and T3-exposed (black bars) cells in accordance with an embodiment.

Figure 4:
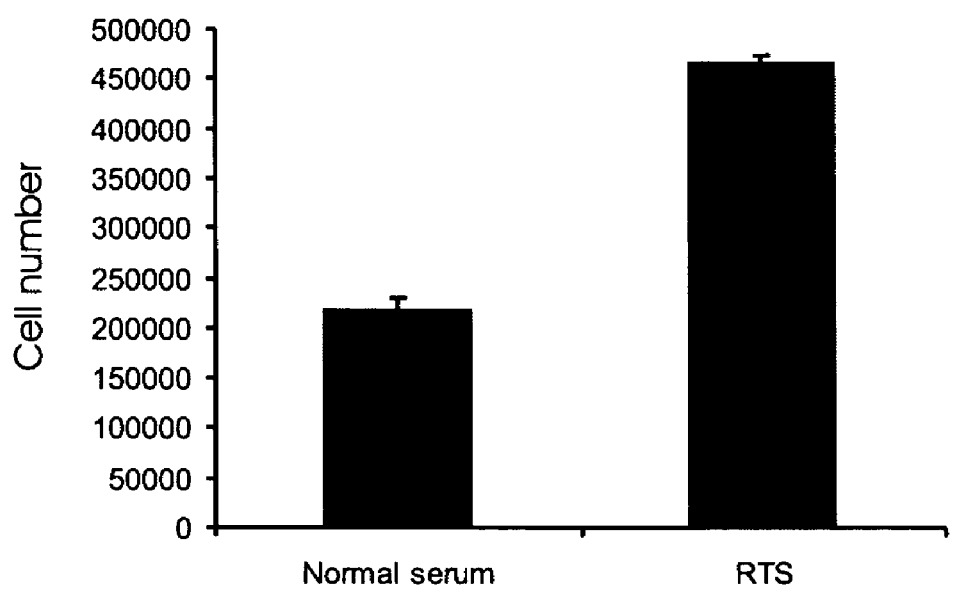

FIG. 4 is evidence that RTS is suitable for growth and maintenance of cell cultures. $3.5 \times 10^4$ XTC cells were plated in quadruplicate 6 well plates and cultured in the presence of medium containing either 10% normal serum or *Rana catesbeiana* tadpole serum (RTS). After 7 days, the cells trypsinized and counted on a hemocytometer. The total cell numbers are indicated in accordance with an embodiment.

Figure 5:
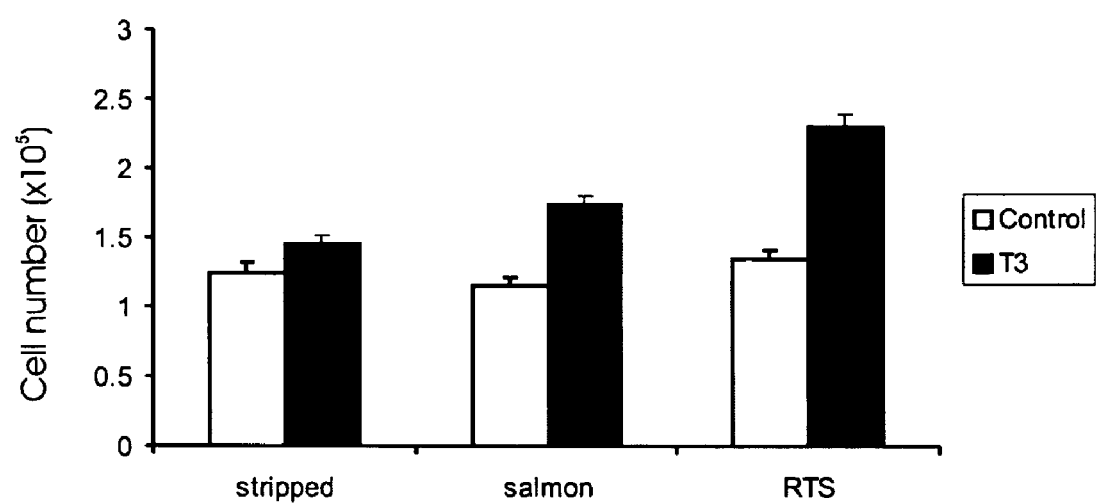

FIG. 5 is evidence that serum from other species is suitable for use in thyroid hormone induction experiments with mammalian cells. $3.5 \times 10^4$ rat pituitary GH3 cells were plated in duplicate at a density of $2 \times 10^4$ cells/cm$^2$ and cultured in the presence of medium containing either 10% charcoal stripped fetal calf serum (stripped), serum from salmon parr (salmon), or *Rana catesbeiana* tadpoles (RTS). After 2 days, 10 nM T3 or vehicle control was added and the cells were counted 5 days later after trypsinization on a hemocytometer. The total cell numbers are indicated with vehicle control (white bars) and T3-exposed (black bars) cells in accordance with an embodiment.

Figure 6:
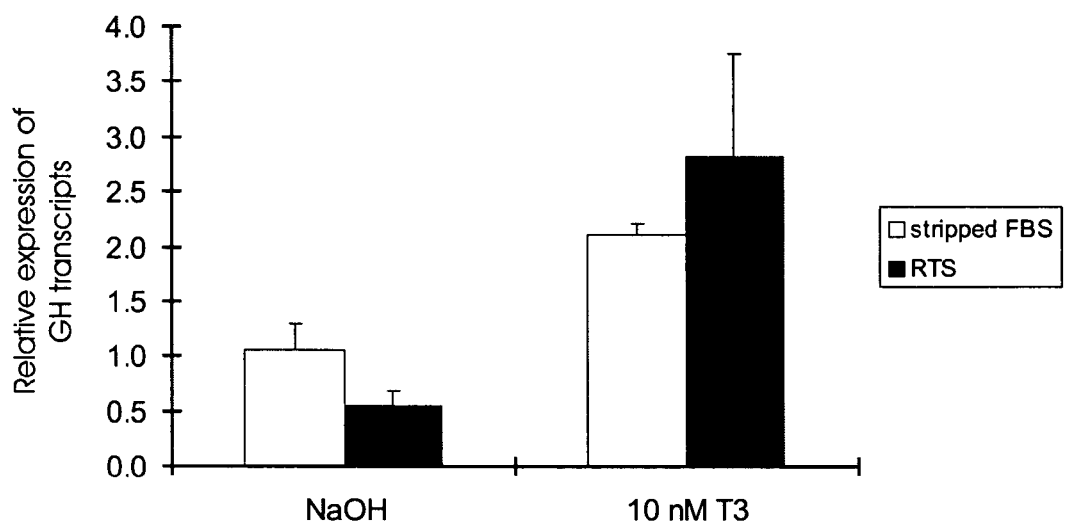
Figure 6:
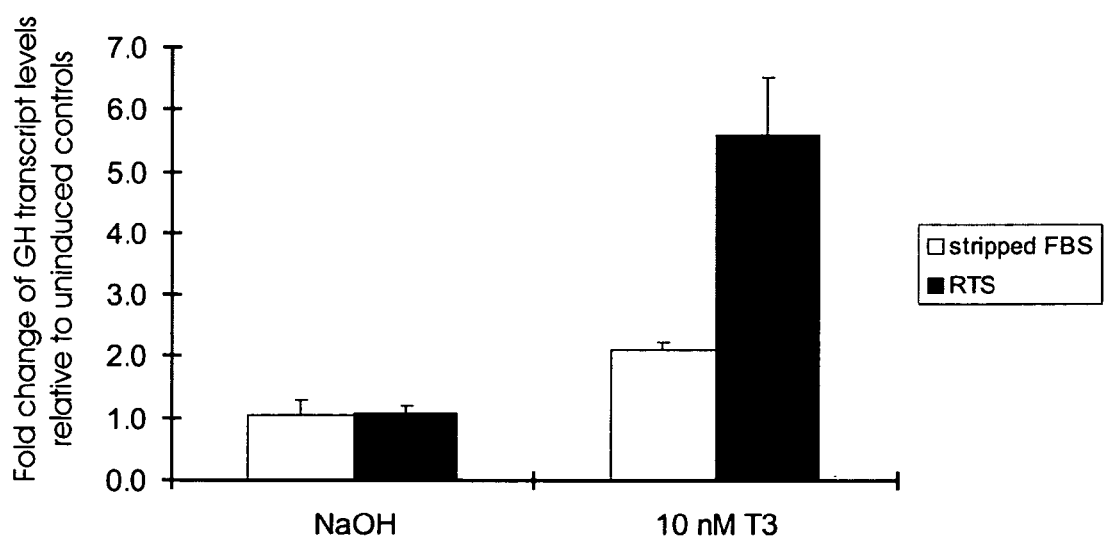

FIG. 6 is showing that GH3 mammalian cells cultured in *Rana catesbeiana* tadpole serum have lower background levels of growth hormone (GH) mRNA transcript compared to charcoal stripped serum. The indicated cell types were plated at a density of $2 \times 10^4$ cells/cm$^2$ and cultured in the presence of medium containing either 10% charcoal stripped fetal calf serum (stripped) or *Rana* tadpole serum (RTS). After 2 days, 10 nM T3 or vehicle control was added and the cells were harvested 2 days later for quantitative real time-polymerase chain reaction (RT-QPCR) analysis for GH transcript levels (indicative of the presence of thyroid hormones). All values were normalized to an invariant L8 ribosomal protein transcript. A) Relative expression levels of the control cells. B) Fold change of the GH transcript levels relative to the control, uninduced cells in accordance with an embodiment.

DETAILED DESCRIPTION

A low thyroid hormone serum supplemented medium, its production and its use is described by way of examples. The serum can be isolated from any vertebrate animal whose developmental stages naturally have serum with low T3 and T4 levels.

DEFINITIONS

Fish
Fish include the Salmonidae such as *Salmo salar* (Atlantic salmon), *Oncorhynchus kisutch* (coho salmon), *O. tshawytcha*, (Chinook salmon), *O. rhodurus* (amago salmon), *O. keta* (chum salmon), *O. nerka* (sockeye salmon), *O. gorbuscha* (pink salmon), *O. mykiss* (rainbow trout), *Salvelinus alpinus* (arctic char); members of the Order Pleuronectiformes such as *Scophthalmus* and *Pleuronichthys* spp. (turbot), *Verasper* Spp. (halibut), *Solea* and *Pleuronectes* spp. (sole and plaice), *Platichthys* spp. (flounder), *Hippoglossus* spp. (brill), and *Lepidorhombus* and *Reinhardtius* spp. (scaldfish); and members of the *Petromyzontiformes* (lampreys).

Anura
Anura (Salientia) include frogs and toads such as the Ranidae (riparian frogs) exemplified by *Rana catesbeiana* (North American bullfrog), *R. clamitans* (green frog), *R. grylio* (pig frog), *R. esculenta* (edible frog), *R. temporaria* (common frog), *R. pipiens* (leopard frog), *R. guentheri* (asian frog), *R. erythraea* (common green frog); members of the Bufonidae (true toads) exemplified by *Bufo bufo* (common toad) and *Bufo marinus* (cane toad); members of the Hylidae (tree frogs); members of the Pelobatidae (spadefoot toads); and members of the Pipidae (tongueless frogs) exemplified by *Xenopus laevis* (South African clawed frog) and *Xenopus* (Silurana) *tropicalis* (western clawed frog).

Urodela
Urodela (Caudata) include salamanders, mudpuppies, and newts such as the Salamandroidea exemplified by *Ambystoma tigrinum* (tiger salamander), *Necturus maculosus* (mudpuppy), and *Ambystoma mexicanum* (Mexican axolotl).

Thyroid Hormone Responsive Cells
The cells can be, for example, but not limited to mammalian, other vertebrate (for example frog or fish), or invertebrate (for example *Spodoptera frugiperda* ovarian cells, Sf9, Sf21). The invertebrate cells are susceptible to baculovirus infection for the production of recombinant thyroid hormone binding proteins in the absence of thyroid hormones in methods that are known to those trained in the art.

The cells can be attached to the culture dish or suspension cultures. The invention can be added to medium for the use of attached cells or to medium for the use of suspension culture.

GH3, GH1, GC: all are derived from rat pituitary epithelial cells. These cells are adherent, growing in clusters. They respond to thyroid hormone by producing growth hormone (through enhancement of gene expression and production of the protein) and by proliferating.

XTC-2, XL-58, XL2, A6, XL177, XLA, XLT-15: all are derived from *Xenopus laevis* from various tissue sources and are adherent. All are thyroid hormone responsive and respond by changing gene expression such as elevation of TRβ, basic transcription element binding (BTEB), and keratin mRNA transcripts. XLT-15 cells undergo programmed cell death (apoptosis) in the presence of thyroid hormones.

nTERA2 cl. D1: adherent human embryonal carcinoma fibroblast cells that can be induced to differentiate into neurons by retinoic acid. They show varied thyroid hormone responsiveness (based upon gene expression) depending upon differentiation state.

Cells that could be used to introduce thyroid hormone receptors into:
HeLa (human epithelial, adherent)
NIH3T3 (mouse fibroblasts, adherent)
rat 1(a) (rat fibroblasts, adherent)

COS7 (African green monkey fibroblasts, adherent)
Neuro2(a) (mouse neuroblast, adherent)
PC12 (rat pheochromocytoma, loosely adherent, multicell aggregates)
Hs68 (human normal diploid fibroblast, adherent)
CV-1 (African green monkey fibroblast, adherent)
Raji (human B cell lymphoma, suspension)
Daudi (human B cell lymphoma, suspension)
S49 (Thy1a) (mouse T cell lymphoma, suspension)
TK1 (mouse T cell lymphoma, suspension)
Jurkat (human T cell lymphoma, suspension) and
BG-9 (human skin fibroblast cells, adherent)

Cellular Response
1) change in thyroid hormone responsive gene expression (e.g. increase in TRβ, BTEB, growth hormone, decrease in thyroid stimulating hormone)
2) enhanced cell proliferation (e.g. GH3 cells)
3) production of growth hormone (e.g. GH3 cells)
4) induction of apoptosis (e.g. XLT-15 cells)

Growth Hormone
Growth hormone is a protein that is produced by pituitary cells such as GH3 cells in response to thyroid hormone exposure (Seo et al., 1977)

Gene Expression
Gene expression refers to the process whereby the genetic code is transcribed into messenger RNA (mRNA) which may lead to the translation of the mRNA into protein in a process termed translation.

Growth Hormone Production
This includes the synthesis of the mRNA transcript encoding the growth hormone protein and the synthesis of the protein itself. The mRNA transcripts can, for example, be measured by Northern blot, dot blot, hybridization, or polymerase chain reaction by those trained in the art. Growth hormone protein can be measured by Western blot, dot blot, immunoprecipitation, or (enzyme-linked immunosorbent assay) ELISA by those trained in the art (Seo et al., 1977; Coligan et al., 2003; Ausubel et al., 2004).

Enhanced Cell Proliferation
Enhanced cell proliferation refers to an increased rate of growth or cell division. This can be measured, for example, by counting the cells using a hemocytometer (such as the method used in FIG. 5), using a MTT assay, or by flow cytometry by those trained in the art (Bonifacino et al., 2004; Kitamura et al., 2005).

Apoptosis
Apoptosis is a type of programmed cell death that can be measured by, for example, by Annexin V binding to the cell membrane, by TUNEL assay, by assaying for DNA laddering, by a change in mitochondrial potential, by cytochrome C release from mitochondria, by flow cytometry, and by caspase activity assays by those trained in the art (Bonifacino et al., 2004).

Stripping
Removal or reduction of the levels of T3 and T4 from serum. This can be carried out using a wide variety of methods including activated charcoal or AG1-X10 or AG1-X8 resin (e.g. (Samuels, Stanley et al. 1979)). These methods are proposed for example by Lewis and Parsons U.S. Pat. No. 4,431,741 issued Feb. 14, 1984, Eisentraut U.S. Pat. No. 3,776,698 issued Dec. 4, 1973, Turner et al. U.S. Pat. No. 3,922,145 issued Nov. 25, 1975, and Hollander U.S. Pat. No. 3,928,553 issued Dec. 23, 1975. A low affinity antibody to T3 or T4 to reduce the serum concentration of thyroid hormone has also been suggested as in Lewis and Parsons U.S. Pat. No. 4,431,741 issued Feb. 14, 1984. Serum that is not stripped has not had the levels of T3 or T4 or both T3 and T4 reduced in vitro.

Low Thyroid Hormone Levels
Low levels of thyroid hormone are considered to be less than approximately 100 ng/dl total T3 or 5 micrograms/dl total T4 as these are the lower end of normal range for humans and cattle (Samuels, Stanley et al. 1979; Shanker, Rao et al. 1984; Health 2005).

Essentially Zero
Levels of thyroid hormone that are essentially zero are levels that do not induce a measurable cellular response in thyroid hormone responsive cells.

Heat Inactivation
Heat inactivation is meant to inactivate the heat labile complement found in the blood which serves as a defense system in the blood. Heat inactivation may not be necessary since just warming up the serum to working temperature might sufficiently inactivate complement. There is no set temperature or need for this process.

Low Thyroid Hormone Developmental Stage
A low thyroid hormone developmental stage is one wherein the animal has low thyroid hormone levels as defined above. The developmental stages include premetamorphosis and prometamorphosis. Other terms are used as well, for example, in salmonids, the term parr is used, which is a fish prior to smoltification, whereas for flatfish the term larval stage (before metamorphosis into a juvenile) is used. For urodeles, the term refers to the larval stage which can include neotenic individuals. The term neoteny refers to a state where the juvenile characteristics are retained into adulthood. For birds and reptiles, the term is embryonic (they don't undergo metamorphosis) or neotenic stages.

For some urodeles (salamanders), their normal development includes neoteny which is a state where the animal retains its larval characteristics but is able to breed. This is not interchangeable with pre- and prometamorphosis which refers to immature animals that are larvae. However the neotenic stage is often a result of the failure to either produce endogenous thyroid hormones or to respond to the natural surge of endogenous thyroid hormones that would normally result in the metamorphosis of the urodele. Metamorphosis in salamanders is less dramatic than in tadpoles. The most obvious morphological changes are that the external gills and tail fin are lost. Neoteny is a normal life stage for many salamanders. Metamorphosis in all cases can be inhibited by chemical (using goitrogens) or mechanical (surgical thyroid gland removal) means.

Some birds (ratites such as ostriches and emus), are regarded as neotenic birds. Neoteny is typical of all ratites (flightless birds) and is characterized by comparatively long legs and short wings, downy feathers lacking cross-lining barbules, and head structure with typically large eyes (Dawson et al. 1996).

The low thyroid hormone developmental stage can be naturally or artificially induced or maintained.

Overview

Low levels of thyroid hormone are considered to be less than approximately 100 ng/dl total T3, or less than approximately 5 micrograms/dl total T4 or less than approximately 50 ng/dl total T3 and 2.5 micrograms/dl total T4. Serum can be prepared from the vertebrate animals at the developmental stages corresponding to low or no endogenous thyroid hormone. Serum can also be prepared from these vertebrates at other developmental stages by treating the vertebrates in order to reduce or prevent thyroid hormone production and then collecting the serum. Thyroid hormone levels can be further reduced in the serum by stripping the serum.

The examples show that the serum can be used on mammalian and non-mammalian cell lines in experiments to study TH-induced responses. The following is a non-exhaustive list of thyroid hormone responsive cells that can be employed: GH3, GH1, GC, XTC-2, XL-58, XL2, A6, XL177, XLA, XLT-15, and nTERA2 cells.

The results show the serum provides superior background levels and superior TH inducibility characteristics in comparison to stripped serum. The serum can be added to any culture medium, usually accounting for between approximately 1-25% of the total culture volume.

EXAMPLES

Experimental Animals

The care and treatment of animals used in this study were in accordance with the guidelines of the Animal Care Committee at the University of Victoria. Rana catesbeiana tadpoles were either purchased (Ward's Natural Science Ltd, St. Catharines, ON) or caught locally and maintained under natural lighting conditions in a 360 L all-glass flow-through aquarium containing recirculated water that undergoes a multi-step water treatment program which includes particulate filtration, ozone-hydrogen peroxide and UV sterilization and temperature adjustment to 14±1° C. Tadpoles were fed Spirulina (Aquatic Ecosystems Inc, Apopka, Fla.) twice daily. Tadpoles were staged according to (Taylor and Kollros 1946). Atlantic salmon parr (Salmo salar) were obtained from Microtek International and were approximately 10 g in size. Salamanders (Ambystoma mexicanum) were purchased from the University of Manitoba axolotl breeding colony.

Serum Collection

Animals were anaesthetized in 0.1% tricaine methane sulfonate (Syndel Laboratories, Vancouver, BC) buffered with 2.1 g/L sodium bicarbonate (ACP, Montréal, PQ). Blood was collected by using a straight-backed razor blade and cutting perpendicular to the tail at a position proximal to the body. The incision severed the caudal blood vessel, but did not sever the tail completely such that blood could pool in the incision. The blood was collected using a Gilson pipettor and transferred polypropylene tubes. Another method constitutes blood collection by cardiac puncture using an 18 gage needle and transferring the blood to polypropylene tubes. Blood collection can also be by decapitation and collection in a container or venous/arterial puncture and collection in a Vacutainer. Once the blood coagulated (about 10 minutes), it was centrifuged at 1,500×g for 5 minutes and the serum supernatant transferred to a new tube. After filtration through a 0.2 μM filter (Pall Corporation, Ann Arbor, Mich.), the sterilized serum was incubated at 56° C. for 10 min to heat inactivate the complement. This heat inactivation step may not be necessary depending upon the cell type to be cultured with the serum. The serum was then stored at −20° C. until required for use.

Cell Culture

Two frog cell lines, XTC-2 cells (Machuca and Tata 1992) and XLA cells (Kanamori and Brown 1993) were obtained from J. Tata and D. Brown, respectively and grown in 70% Liebovitz medium supplemented with 10% bovine growth serum, 100 g/ml gentamycin sulfate and 10 mM Hepes, pH 7.5 (GIBCO/Invitrogen, Grand Island, N.Y.). These cells were grown at 25° C. in air. The rat pituitary tumor GH3 cell line was obtained from R. T. Zoeller and maintained in Kaighn's modification of Ham's F 12 medium with 2 mM glutamine, 1.5 g/L sodium bicarbonate, 10% fetal bovine serum, 1,000 U/ml penicillin, and 1 mg/ml streptomycin at 37° C. in 5% $CO_2$. Charcoal stripped fetal bovine serum was prepared according to (Samuels, Stanley et al. 1979) and was added to the culture medium to a final concentration of 10% (v/v) (to replace the normal bovine growth serum), but could be added to about 1% to about 25% volume/volume serum to medium, such as about 5% to about 15%, or about 7% to about 12%, such as about 10% volume/volume.

Similarly, the Liebovitz medium with additives or the Ham's F12 medium with additives were prepared as indicated above except the bovine growth serum was replaced with serum from either Rana catesbeiana tadpole serum (RTS), salmon parr serum, or salamander serum to a final concentration of 10% (v/v), but could be added to about 1% to about 25% volume/volume serum to medium, such as about 5% to about 15%, or about 7% to about 12%, such as about 10% volume/volume.

The culture medium includes about 0 to about 10 ng/dl total T3, and about 0 to about 0.5 micrograms/dl total T4, and may contain at most about 5 ng/dl total T3 and about 0.25 micrograms/dl total T4, or essentially no thyroid hormone.

For cell counting, the frog cells were briefly washed in CMFM (88 mM NaCl, 1 mM KCl, 2.4 mM $NaHCO_3$, 7.5 mM Tris HCl, pH 7.6) and removed from the culture dish with 0.05% (w/v) trypsin/0.5 mM EDTA. The trypsinized cells were centrifuged at 1,500×g at room temperature and resuspended in the appropriate medium with additives. The GH3 cells were treated in the same way except they were washed with phosphate-buffered saline (138 mM NaCl, 2.7 mM KCl, 10.1 mM $Na_2HPO_4$, 1.8 mM $KH_2PO_4$) before trypsinization.

Total RNA Isolation and cDNA Preparation

Cultured cells were homogenized in the presence of TRIzol reagent as described by the manufacturer (Invitrogen Canada Inc, Burlington, ON). Isolated total RNA was subsequently resuspended in diethyl pyrocarbonate (DEPC)-treated RNase-free water and stored at −70° C. The total RNA yield for each sample was determined by spectrophotometry at 260 nm. cDNA was synthesized by annealing one microgram of total RNA with 500 ng random hexamer oligonucleotide (Amersham Biosciences Inc, Baie d'Urfé, QC) at 65° C. for ten minutes followed by a quick cool-down on ice. RNA was converted to cDNA using 200 units of MMLV RNase H⁻ Superscript II reverse transcriptase as described in the manufacturer's recommended protocol (Invitrogen Canada Inc, Burlington, ON). The 20 μl reaction was incubated at 42° C. for two hours and diluted 20-fold prior to DNA amplification.

Real-Time Quantitative Polymerase Chain Reaction (QPCR).

The expression of TRβ and GH gene transcripts was analyzed using a MX4000 real-time quantitative polymerase chain reaction system (Stratagene, La Jolla, Calif., USA) as described previously (Crump, Werry et al. 2002) using gene specific primers (for TRβ: UP primer 5'-TAACAAGAAAC-CAGTGCCAAGA; DOWN primer 5'-GAGCGACAT-GATCTCCATACAA; for GH: UP primer 5'-GAGCGTGC-CTACATTCCC; DOWN primer 5'-TTGAGCAGAGCGTCATCG). The annealing temperature was 55° C. A standard curve for each primer pair was generated using the appropriate quantified plasmid DNA containing the target gene sequence. Quadruplicate reactions were performed for each sample and data were averaged and normalized to the expression of the control gene encoding the ribosomal protein L8.

Results and Discussion

Cell lines that are responsive to TH action include the frog cell lines, XTC-2 cells (Machuca and Tata 1992) and XLA cells (Kanamori and Brown 1993) and the rat pituitary tumor GH3 cell line. The frog cell lines respond to TH by up-regulating the activities of several genes in a hormone-dependent manner. TH receptor β (TRβ) gene expression is used as a standard marker for the presence of TH as this gene is a direct target for up-regulation by TH (Machuca, Esslemont et al. 1995). The GH3 cell line is widely used as a standard pituitary model where cell proliferation and growth hormone secretion is dependent upon TH (Perrone, Greer et al. 1980; Kitagawa, Obata et al. 1987). This cell line is also being developed as a test for TH disrupting chemicals (Kitamura, Jinno et al. 2005; Kitamura, Suzuki et al. 2005).

The standard way that TH induction experiments are conducted is as follows: the cells are maintained in medium containing 10% regular bovine serum which is removed and replaced with medium containing 10% stripped bovine serum; they are incubated for 2 days to allow time for acclimation to the reduced TH-containing environment; and after 2 days, the cells are treated with $T_3$ to induce them and are subsequently assayed.

XLA and XTC-2 cells in 6 well tissue culture dishes were seeded at the same density, and incubated in medium containing either 10% stripped bovine serum or serum from premetamorphic *Rana catesbeiana* tadpoles (RTS) for 2 days. Ten nM T3 or solvent control was added to the medium and the cells were incubated for a further 2 days. Total RNA was isolated from these cells and analyzed for the levels of the TRβ gene by reverse transcription quantitative real time polymerase chain reaction (RT-QPCR). All data were normalized to an invariant ribosomal L8 protein gene transcript (Shi and Liang 1994). FIG. 1A shows a comparison between the background control levels of TRβ mRNA in cells grown in charcoal stripped serum-containing medium compared to cells grown in RTS-containing medium. In both cell lines tested, the relative amounts of TRβ transcripts are substantially lower in cells that are grown in RTS-containing medium. This is indicative of higher levels of THs in the stripped serum compared to RTS.

When these cells were exposed to T3, the TRβ mRNA levels increase in a well-characterized response (FIG. 1B). However, the degree of induction was much greater in the presence of RTS.

In order to test the range of developmental stages that are suitable for serum production, serum from two premetamorphic (TK stage VI and XII; (Taylor and Kollros 1946)) and two prometamorphic (TK stage XV and XVIII) stages of *Rana catesbeiana* were tested (FIG. 2). In all cases where RTS was used, regardless of the stage of animal, the baseline TRβ mRNA expression levels in the XTC cells were lower than those grown in the charcoal stripped-fetal calf serum. Addition of 10 nM T3 elicited a robust elevation in TRβ levels in all cases. Since the baseline levels were much lower in the cells exposed to RTS, the fold induction was higher with RTS.

To test the broader applicability of this approach to using serum from other species, we tested serum from salmon parr and neotenic salamanders (FIG. 3) on the inducibility of TRβ transcripts in XTC cells in the same manner as in FIG. 2. These data show that serum from both sources support an accumulation of TRβ transcript in the presence of 10 nM T3 compared to uninduced controls. The difference in induced TRβ transcript levels between the experiments shown in FIGS. 2 and 3 in the cells grown in the charcoal stripped serum-containing medium accentuates the variability in batches of serum prepared in this way.

The ability of RTS to support the growth and maintenance of cultured XTC cells over a longer period of time was also tested (FIG. 4). Not only did the cells grow extremely well with RTS, they out-performed growth in normal growth medium.

The ability of serum from non-mammalian sources to support a TH-induced acceleration of growth in mammalian cells commonly used for TH studies was evaluated. We used rat pituitary GH3 cells to evaluate the standard TH-induced response of increased proliferation (Kitagawa, Obata et al. 1987). After 7 days, the cells tripled in number in the charcoal-stripped fetal calf serum, salmon parr serum, and RTS (FIG. 5). When the cells were exposed to 10 nM T3, all three sera showed increased proliferation relative to the vehicle controls, but the effect was most marked when the cells were T3-induced in the presence of the non-mammalian sera (FIG. 5). This is suggestive that the non-mammalian sera contain additional factors that may have been removed from the stripped serum that better support a more robust TH-induced proliferative response.

Finally, FIG. 6A shows a comparison between the background control levels of GH mRNA in rat GH3 cells grown in charcoal stripped serum-containing medium compared to cells grown in RTS-containing medium. The relative amounts of GH transcripts are substantially lower in cells that are grown in RTS-containing medium. This is indicative of higher levels of THs in the stripped serum compared to RTS.

When these cells were exposed to T3, the GH mRNA levels increase in a well-characterized response (FIG. 6B). However, the degree of induction was much greater in the presence of RTS.

Taken together, these data support the use of non-mammalian, vertebrate serum for cell culture where TH levels need to be low.

The foregoing is a description of an embodiment. As would be known to skilled in the art, variations that do not alter the scope would be contemplated. For example, but not to be limiting, the medium could be any culture medium used to support cell growth or used to assay cell responses, the serum can be collected from vertebrates that have low endogenous thyroid hormone levels, or no endogenous thyroid hormones and the serum can be added to any concentration, although usually it is added to provide approximately 1-25% serum in the culture medium. Also, cells that have thyroid hormone receptor introduced into them (by transfection, electroporation, or other methods) can be employed. Expression could be transient or stable. Further, cells that are cultured from TR knockout mice are also contemplated. Still further, as there are multiple TR forms known, it is also contemplated that cell lines that have or do not have part of a TR protein are contemplated. Cellular responses can include, for example, but not limited to growth hormone changes, gene expression, cellular proliferation and apoptosis.

REFERENCES

Crump, D., K. Werry, et al. (2002). "Exposure to the herbicide acetochlor alters thyroid hormone-dependent gene expression and metamorphosis in *Xenopus laevis*." Environ Health Perspect 110(12): 1199-205.

Dickhoff, W. W. and C. V. Sullivan (1987). "Involvement of the thyroid gland in smoltification, with special reference to metabolic and developmental processes." *American Fish Society Symposium* 1: 197-210.

Eales, J. G. and S. B. Brown (1993). "Measurements and regulation of thyroidal status in teleost fish." *Rev Fish Biol Fish* 3: 299-347.

Health, U. S. N. L. o. M. a. N. I. o. (2005). T3 and T4 tests, U.S. National Library of Medicine and National Institutes of Health. 2005.

Inui, T. and K. Miwa (1985). "Thyroid hormone induces metamorphosis in flounder larvae." *Gen Comp Endocrinol* 60: 450-454.

Kaltenbach, J. C. (1996). Endocrinology of amphibian metamorphosis. *Metamorphosis: postembryonic reprogramming of gene expression in amphibian and insect cells*. L. I. Gilbert, J. R. Tata and B. G. Atkinson. San Diego, Academic Press: 403-431.

Kanamori, A. and D. Brown (1993). "Cultured cells as a model for amphibian metamorphosis." *Proceedings of the National Academy of Sciences (USA)* 90: 6013-6017.

Kitagawa, S., T. Obata, et al. (1987). "Thyroid hormone action: induction of morphological changes and stimulation of cell growth in rat pituitary tumor GH3 cells." *Endocrinology* 120: 2591-2596.

Kitamura, S., N. Jinno, et al. (2005). "Thyroid hormone-like and estrogenic activity of hydroxylated PCBs in cell culture." *Toxicology* 208: 377-387.

Kitamura, S., T. Suzuki, et al. (2005). "Comparative study of the endocrine-disrupting activity of bisphenol A and 19 related compounds." *Toxicological Sciences* 84: 249-259.

Machuca, I., G. Esslemont, et al. (1995). "Analysis of structure and expression of the *Xenopus* thyroid hormone receptor beta gene to explain its autoinduction." *Molecular Endocrinology* 9: 96-107.

Machuca, I. and J. Tata (1992). "Autoinduction of thyroid hormone receptor during metamorphosis is reproduced in *Xenopus* XTC-2 cells." *Molecular and Cellular Endocrinology* 87: 105-113.

Norris, D. O. (1997). *Vertebrate Endocrinology*. San Diego, Calif., Academic Press.

Perrone, M. H., T. L. Greer, et al. (1980). "Relationships between thyroid hormone and glucocorticoid effects in GH3 pituitary cells." *Endocrinology* 106: 600-605.

Regard, E., A. Taurog, et al. (1978). "Plasma thyroxine and triiodothyronine levels in spontaneously metamorphosing *Rana catesbeiana* tadpoles and in adult anuran amphibia." *Endocrinology* 102: 674-684.

Safi, R., A. Begue, et al. (1997). "Thyroid hormone receptor genes of neotenic amphibians." *Journal of Molecular Evolution* 44: 595-604.

Samuels, H., F. Stanley, et al. (1979). "Depletion of L-3,5,3'-triiodothyronine and L-thyroxine in euthyroid calf serum for use in cell culture studies of the action of thyroid hormone." *Endocrinology* 105: 80-85.

Shanker, G., G. S. Rao, et al. (1984). "Investigations on myelinogenesis in vitro: regulation of 5'-nucleotidase activity by thyroid hormone in culture of dissociated cells from embryonic mouse brain." *Journal of Neuroscience Research* 11: 263-270.

Shi, Y. and V. Liang (1994). "Cloning and characterization of the ribosomal protein L8 gene from *Xenopus laevis*." *Biochimica et Biophysica Acta* 1217: 227-228.

Specker, J. L. (1988). "Preadaptive role of thyroid hormones in larval and juvenile salmon: growth, the gut and evolutionary considerations." *Amer Zool* 28: 337-349.

Taylor, A. C. and J. J. Kollros (1946). "Stages in the normal development of *Rana pipiens* larvae." *Anatomical Record* 94: 7-24.

White, B. A. and C. S. Nicoll (1981). Hormonal control of amphibian metamorphosis. *Metamorphosis: a problem in developmental biology*. L. I. a. F. Gilbert, E. New York, Plenum Publishing.

Yen, P. M. (2001). "Physiological and molecular basis of thyroid hormone action." *Physiological Reviews* 81(3): 1097-1142.

Youson, J. and S. Sower (2001). "Theory on the evolutionary history of lamprey metamorphosis: role of reproductive and thyroid axes." *Comparative Biochemistry and Physiology B Biochemistry and Molecular Biology* 129: 337-345.

I claim:

1. A composition for culturing cells, comprising a culture medium and about 1% to about 25% volume/volume (v/v) serum from an amphibian, a bird at a neotinic stage of development or a ratite, wherein said serum is collected from the amphibian, the bird, or the ratite at a developmental stage with low endogenous thyroid hormone levels, and wherein said composition comprises 10 ng/dl or less 3,5,3'-triiodothyronine (T3) and about 0.5 micrograms/dl or less thyroxine (T4).

2. The composition of claim 1, wherein the composition comprises about 5 ng/dl or less T3 and 0.25 micrograms/dl or less T4.

3. The composition of claim 1, wherein said serum is about 10% (v/v) of the composition.

4. A composition for culturing cells, comprising a culture medium and about 1% to about 25% volume/volume serum from an amphibian, wherein the amphibian is a premetamorphic amphibian or a prometamorphic amphibian, wherein said serum is collected from the amphibian at developmental stage with low endogenous thyroid hormone levels, and wherein said composition comprises 10 ng/dl or less T3 and about 0.5 micrograms/dl or less T4.

5. The composition of claim 4 wherein the amphibian is a frog tadpole.

6. The composition of claim 5, wherein the frog is *Rana catesbeiana*.

7. The composition of claim 4, wherein said amphibian is a neonate amphibian.

8. The composition of claim 7, wherein said neonate amphibian is a salamander *Ambystoma mexicanum* (Mexican axolotl).

9. The composition of claim 4, wherein the composition comprises about 5 ng/dl or less T3 and 0.25 micrograms/dl or less T4.

10. The composition of claim 4, wherein said serum is about 10% (v/v) of the composition.

11. A composition for culturing cells, comprising a culture medium and about 1% to about 25% volume/volume serum from an amphibian, a bird at a neotinic stage of development or a ratite, wherein said serum is collected from the amphibian, the bird, or the ratite at a developmental stage with low endogenous thyroid hormone levels, and wherein the composition comprises essentially 0 ng/dl T3 and essentially 0 micrograms/dl T4.

12. A method of studying a thyroid hormone induced cellular response in vitro, comprising
culturing a thyroid hormone-responsive cell in the composition of claim 1 to form a cell culture; and
adding T3, T4, or both T3 and T4 to the cell culture; and
measuring a cellular response of the thyroid-hormone responsive cell following the adding of T3, T4 or both T3 and T4,
thereby studying a thyroid hormone induced cellular response in vitro.

13. The method of claim 12, wherein the cellular response is cell growth.

14. The method of claim 12, wherein the cellular response is the production of mRNA encoding a growth hormone.

15. The method of claim 12, wherein the cellular response is TH receptor β expression.

16. The method of claim 12, wherein the cell is a frog cell.

17. The method of claim 12, wherein the cell is a rat, mouse, human or monkey cell.

18. The method of claim 12, wherein the composition comprises amphibian serum, wherein said amphibian is a neonate amphibian.

19. The method of claim 12, wherein the composition comprises ratite serum.

20. The method of claim 12, wherein the composition comprises serum from a bird at a neotinic stage of development.

21. A method of studying a thyroid hormone induced cellular response in vitro, comprising
culturing a thyroid hormone-responsive cell in the composition of claim 4 to form a cell culture; and
adding T3, T4, or both T3 and T4 to the cell culture; and
measuring a cellular response of the thyroid-hormone responsive cell following the adding of T3, T4 or both T3 and T4,
thereby studying a thyroid hormone induced cellular response in vitro.

22. The method of claim 21, wherein the cellular response is cell growth.

23. The method of claim 21, wherein the cellular response is the production of mRNA encoding a growth hormone.

24. The method of claim 21, wherein the cellular response is TH receptor β expression.

25. The method of claim 21, wherein the cell is a frog cell.

26. The method of claim 21, wherein the cell is a rat, mouse, human or monkey cell.

27. The method of claim 21, wherein said amphibian is a premetamorphic amphibian.

* * * * *